(12) United States Patent
Yau et al.

(10) Patent No.: US 7,229,283 B2
(45) Date of Patent: Jun. 12, 2007

(54) DENTAL CAST SCANNING APPARATUS

(75) Inventors: Hong-Tzong Yau, Chiayi County (TW); Tsung-Tung Hsieh, Nantou County (TW); Chuan-Chu Kuo, Chiayi County (TW); Jiun-Ren Chen, Yunlin County (TW)

(73) Assignee: Pou Yuen Technology Co., Ltd., Chang Hwa Hsien (TW)

( * ) Notice: Subject to any disclaimer, the term of this patent is extended or adjusted under 35 U.S.C. 154(b) by 326 days.

(21) Appl. No.: 11/052,781

(22) Filed: Feb. 9, 2005

(65) Prior Publication Data

US 2006/0177794 A1    Aug. 10, 2006

(51) Int. Cl.
*A61C 1/14*    (2006.01)
(52) U.S. Cl. ........................................ 433/49
(58) Field of Classification Search .................. 433/49, 433/50, 53, 213, 72, 76
See application file for complete search history.

(56) References Cited

U.S. PATENT DOCUMENTS

| 5,338,198 A * | 8/1994 | Wu et al. .................... 433/213 |
| 6,200,135 B1 * | 3/2001 | Hultgren ...................... 433/49 |
| 6,579,095 B2 * | 6/2003 | Marshall et al. ............ 433/213 |

\* cited by examiner

*Primary Examiner*—Melba Bumgarner
(74) *Attorney, Agent, or Firm*—Bacon & Thomas, PLLC

(57) ABSTRACT

A dental cast scanning apparatus is comprised of a base; a single-tooth cast rotating device having a detachable and rotatable first cast-holding jig; a full-teeth cast rotating device having a detachable and rotatable second cast-holding jig; a scanning unit having a scanning probe, an elevator, and a slide rail mounted on the base, for slidable movement along the slide rail; and two swing drivers connected with the single-tooth and full-teeth cast rotating devices. Accordingly, the first and second cast-holding jigs can be driven to swing and rotate with respect to the scanning probe for a predetermined angle to cause efficient and effective scanning outcome.

11 Claims, 10 Drawing Sheets

DENTAL CAST SCANNING APPARATUS

BACKGROUND OF THE INVENTION

1. Field of the Invention

The present invention relates generally to the technology of manufacturing artificial teeth, and more particularly, to a dental cast scanning apparatus.

2. Description of the Related Art

During the operation of a conventional scanning apparatus for creating three-dimensional (3D) models, scan a workpiece to access all of information relating to the workpiece and then proceed to positioning and integration of the information by software to construct a complete 3D model.

As known, the operation of the conventional scanning apparatus is usually done by manual turning or rotating the workpiece, or by placing the workpiece on a jig to manually rotate the jig. However, there are many variables for such manual operation, such as human errors; for example, the deviation of angle that the workpiece is placed, may be incurred by the manual operation to further result in insufficient information while scanning to require more scanning times to further lengthen the overall scanning time and to increase the degree of the complexity of the follow-up process executed by the software, thereby causing not only uneasy control of the quality of the manufacturing process but also inconsistency of the manufacturing process and further making it difficult to do the personnel training for one company.

SUMMARY OF THE INVENTION

The primary objective of the present invention is to provide an improved dental cast scanning apparatus, which greatly reduces human errors and scanning procedures to further shorten the scanning time and to facilitate the personnel training of one company.

The foregoing objective of the present invention is attained by the improved dental cast scanning apparatus, which is comprised of a base, a single-tooth cast rotating device, a full-teeth cast rotating device, a scanning unit, and two swing drivers. The single-tooth cast rotating device includes a detachable and rotatable first cast-holding jig. The full-teeth cast rotating device includes a detachable and rotatable second cast-holding jig. The scanning unit includes a scanning probe, an elevator, and a slide rail mounted on the base, for slidable movement along the slide rail. The two swing drivers are connected with the single-tooth and full-teeth cast rotating devices. Accordingly, the first and second cast-holding jigs can be driven to swing and rotate with respect to the scanning probe for a predetermined angle to cause efficient and effective scanning outcome.

DETAILED DESCRIPTION OF PREFERRED EMBODIMENTS

Figure 1:
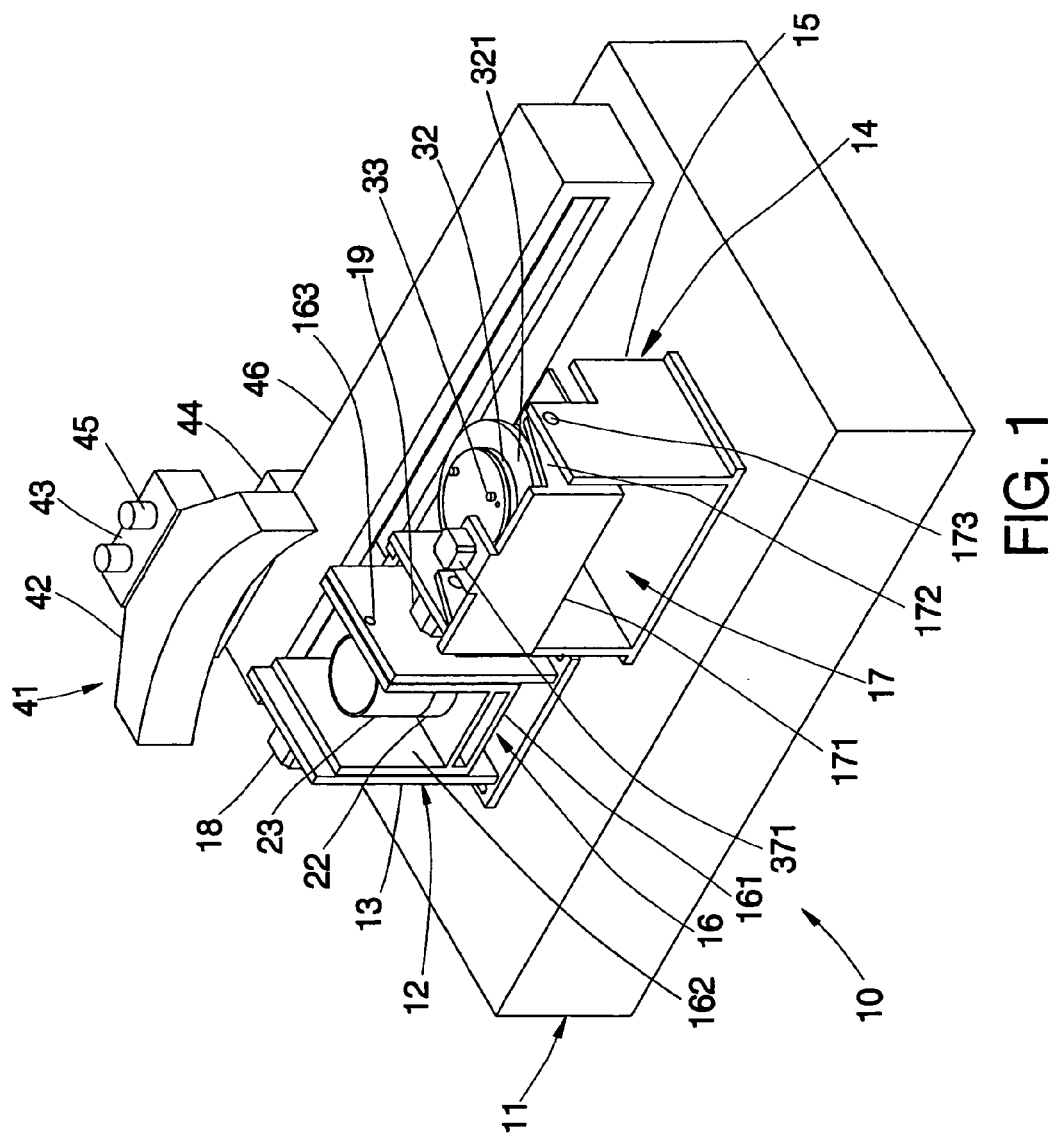
FIG. 1 is a perspective view of a first preferred embodiment of the present invention.
Figure 2:
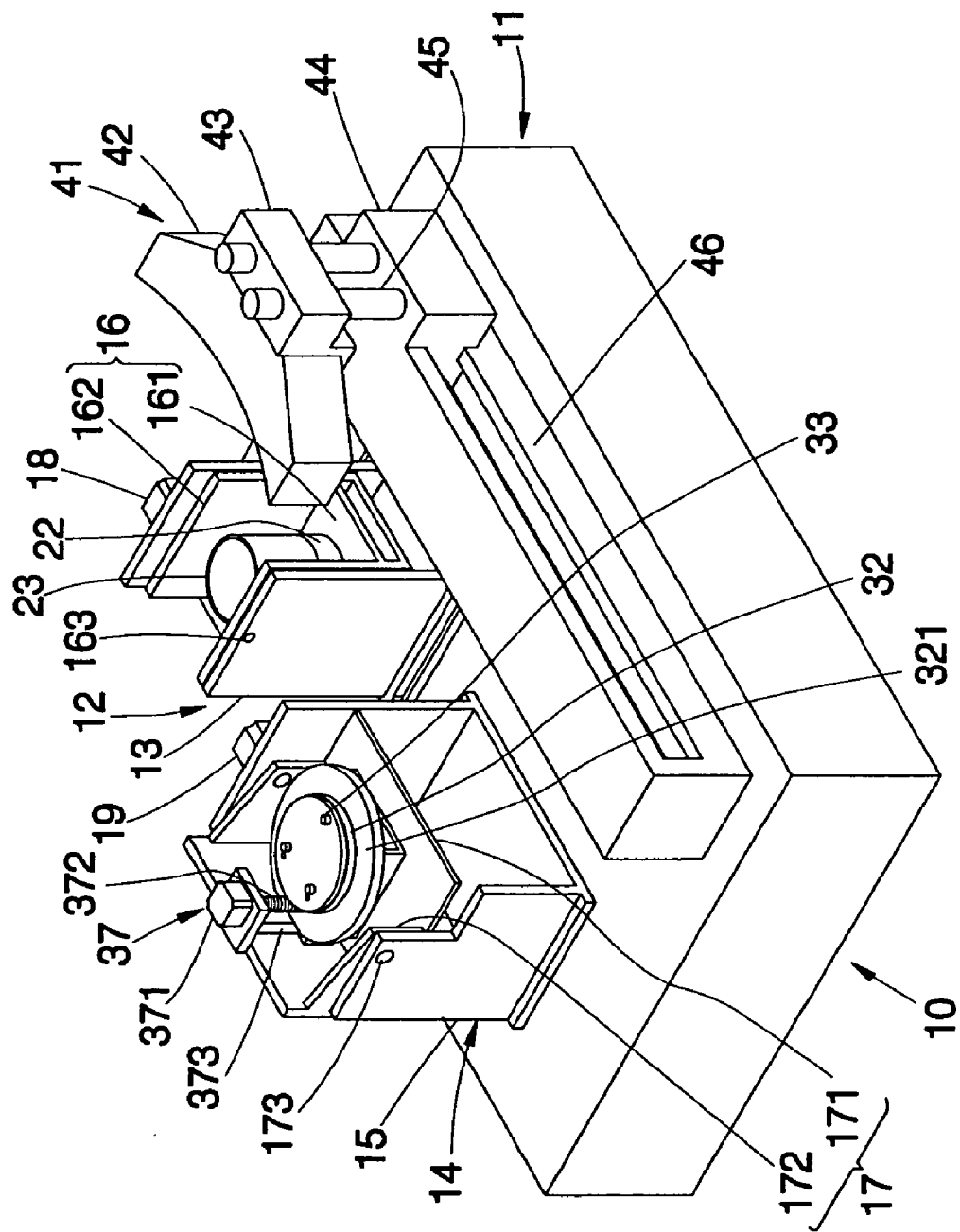
FIG. 2 is similar to FIG. 1, but viewing from the rear side of the present invention.
Figure 3:
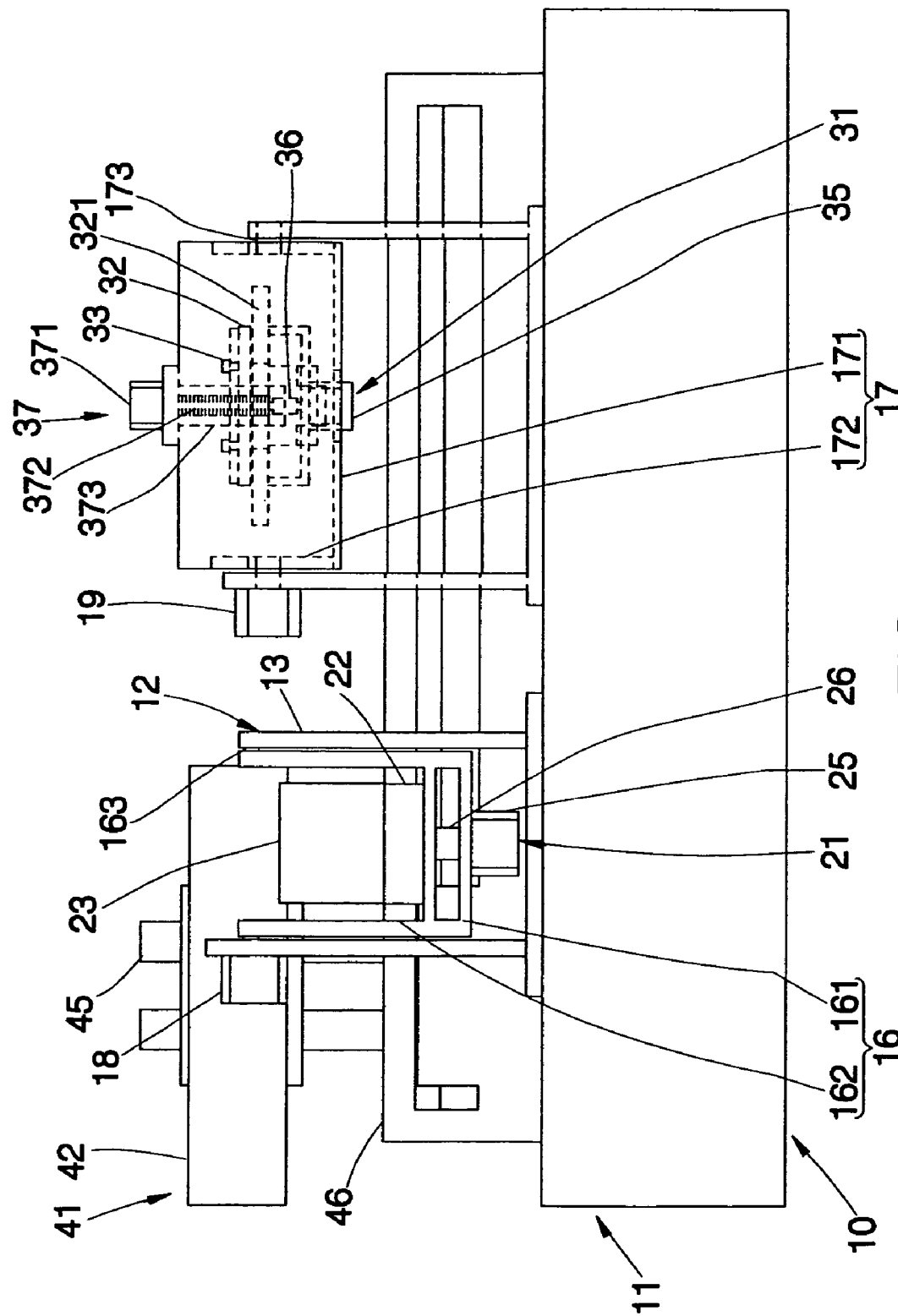
FIG. 3 is a front view of the first preferred embodiment of the present invention.
Figure 4:
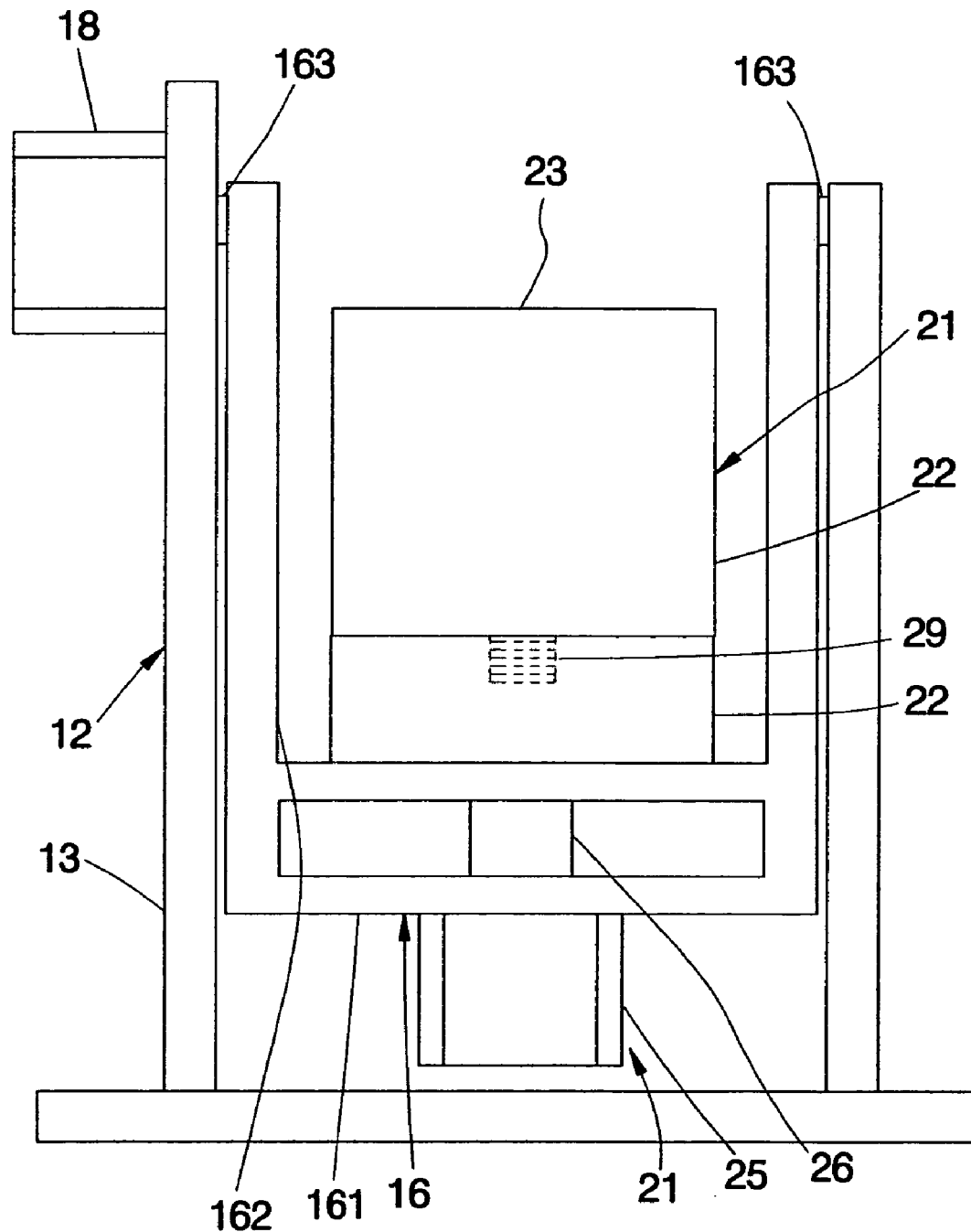
FIG. 4 is a front view of the single-tooth cast rotating device of the first preferred embodiment of the present invention.
Figure 5:
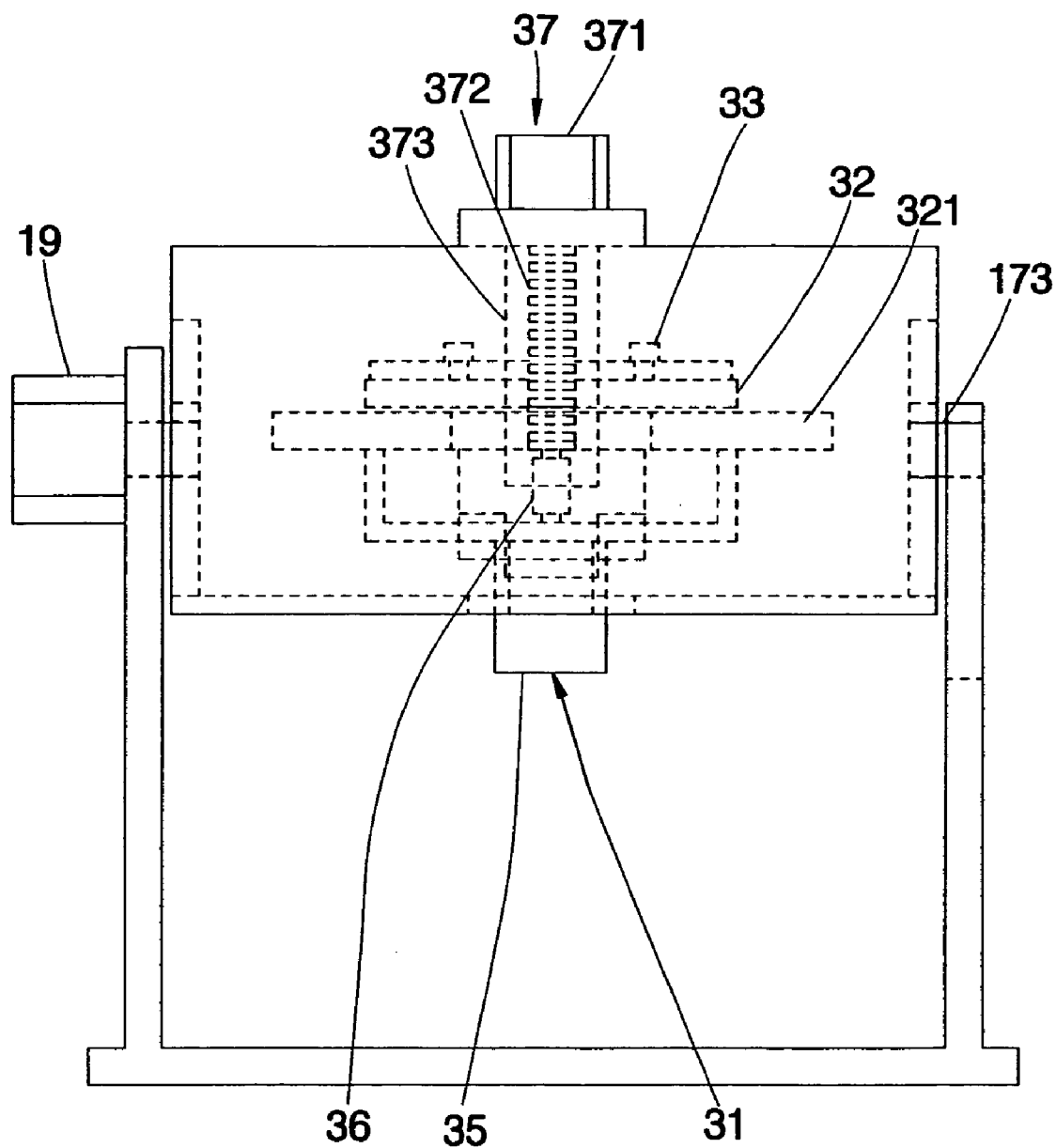
FIG. 5 is a front view of the full-teeth cast rotating device of the first preferred embodiment of the present invention.

Referring to FIGS. 1–5, a dental cast scanning apparatus 10 constructed according to a first preferred embodiment of the present invention is comprised of a base 11, a single-tooth cast rotating device 21, a full-teeth cast rotating device 31, and a scanning unit 41.

A first rack 12 and a second rack 14 are mounted on the base 11, each having two plate-like members 13(15). The two plate-like members 13(15) are spaced from each other for a predetermined distance and mounted upright on the base 11. A U-shaped first swing shelf 16 and a U-shaped second swing shelf 17, each of which has a base plate 161(171) and two side plates 162(172), each are swung between the two plate-like members 13(15) by a pivot bolt 163(173) pivotally interconnecting top ends of the side plates 162(172) and the plate-like members 13(15), for swing driven by an external force with respect to the two racks 12 and 14. The two base plates 161 and 171 of the two swing shelves 16 and 17 are spaced from the base 11 for a predetermined distance. A first swing driver 18 and a second swing driver 19, which are respectively two driving motors in this embodiment, each are mounted on one of the two side plates 13(15) and connected with the pivot bolt 163(173), for respectively driving the two swing shelves 16 and 17 to swing.

The single-tooth cast rotating device 21 includes a first rotatable holder 22 and a first rotation driver 25. The first rotation driver 25 is mounted under the base plate 161 of the first swing shelf 16, having a driving shaft 26 running through the base plate 161 and connected with a bottom side of the first rotatable holder 22, for driving the first rotatable holder 22 to rotate for a predetermined angle. The first rotatable holder 22 has a detachable first cast-holding jig 23, which is a cup-like member in this embodiment. The first cast-holding jig 23 has its bottom side threadedly connected with the first rotatable holder 22 by a screw bolt 20, for fixedly receiving a single-tooth cast for scanning.

The full-teeth cast rotating device 31 includes a workbench 321, a second rotatable holder 32 mounted on the workbench 321 and having a second cast-holding jig 33 on its top side for receiving a full-teeth cast (not shown), a second rotation driver 35 mounted to a bottom side of the workbench 321 and having a driving shaft 36 connected with the second rotatable holder 32 for driving the second rotatable holder 32 to rotate for a predetermined angle, and a lifting-and-lowering driver 37 having a motor 371, a screw rod 372, and a slide rail 373. The motor 371 is mounted to the second swing shelf 17. The screw rod 371 has an end connected with the motor 371 and a body portion thereof threadedly connected with a side of the workbench 321. The slide rail 373 is mounted on the second swing shelf 17. The workbench 321 is slidably mounted to the slide rail 373 to be driven by the motor 371 to move in elevation.

The scanning unit 41 includes a scanning probe 42, a movable member 43 connected with a rear end of the scanning probe 42, an elevator 44, and a slide rail 46. The slide rail 46 is linear in this embodiment, mounted on the base 11, and located beside the single-tooth and full-teeth cast rotating devices 21 and 31. The elevator 44 is a pneumatic cylinder in this embodiment and mounted to the slide rail 46 for reciprocating movement along the slide rail 46, having a piston rod 45 connected with the movable member 43, for driving the scanning probe 42 to move in elevation and to reciprocate together with the elevator 44.

Figure 6:
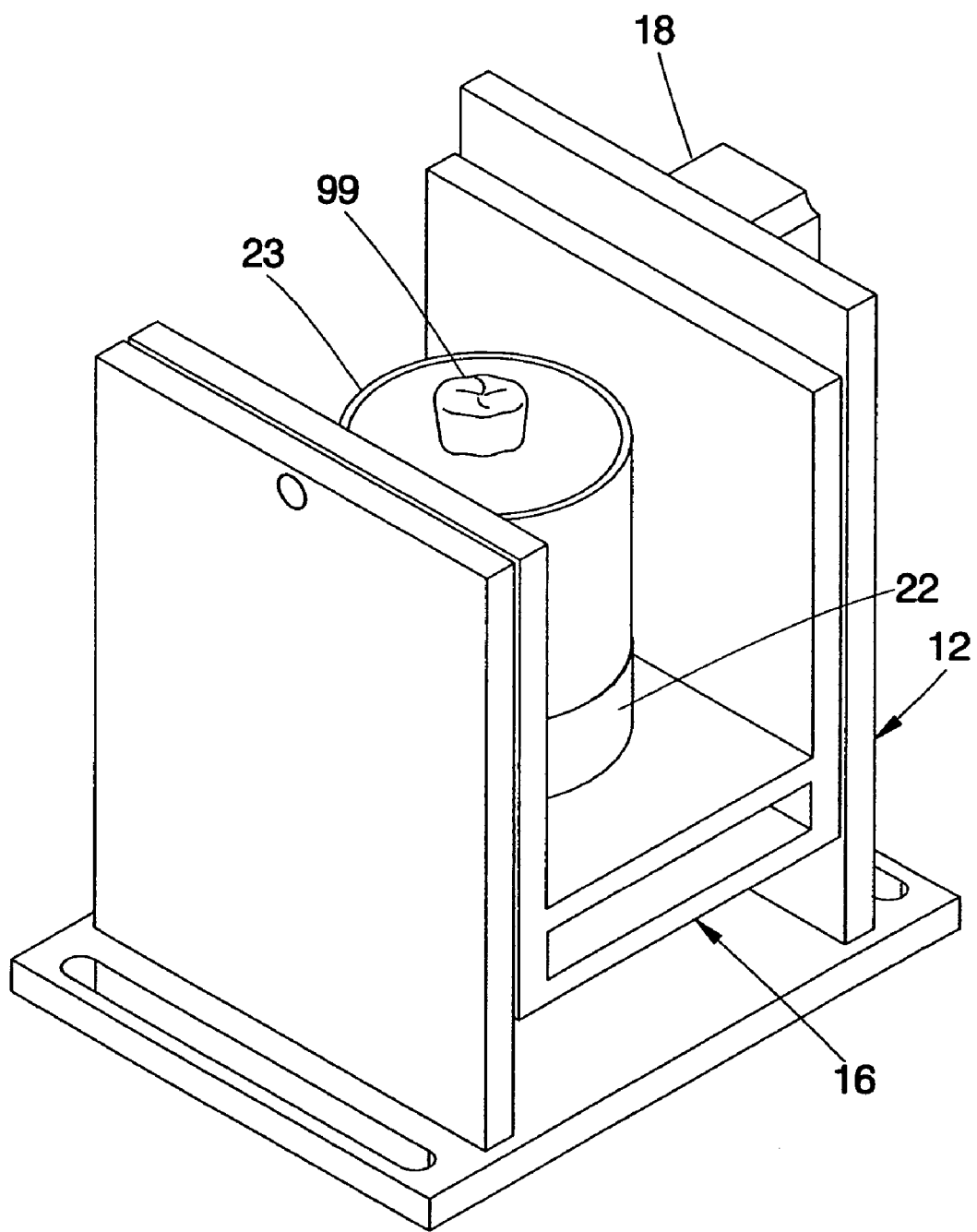
FIG. 6 is a schematic view of the first preferred embodiment of the present invention in operation, showing that a single-tooth cast is placed on the single-tooth cast rotating device.
Figure 7:
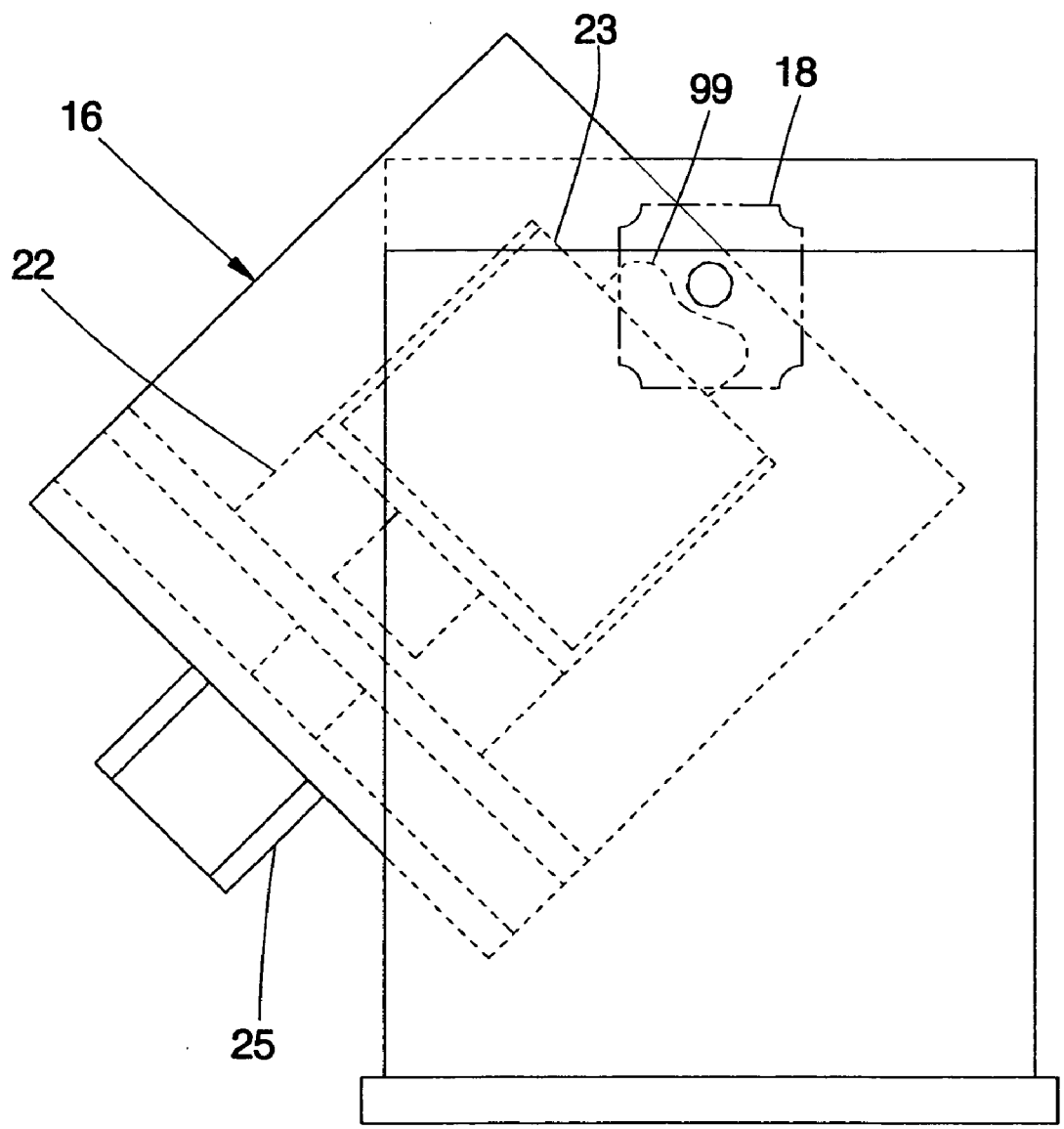
FIG. 7 is another schematic view of the first preferred embodiment of the present invention in operation, showing that the single-tooth cast rotating device is rotating for a predetermined angle.

Referring to FIGS. 1–5 again and FIG. 6, while operating the dental cast scanning apparatus 10, the user can place either a single-tooth cast 99 on the first cast-holding jig 23 or a full-teeth cast (not shown) on the second cast-holding jig 33 as required and then drive the scanning probe 42 to move within the range where the single-tooth cast 99 or the full-teeth cast (not shown) is located for scanning. Taking the single-tooth cast 99 placed on the single-tooth cast rotating device 21 as an example, drive the first rotatable holder 22 for rotation by the first rotation driver 25 to further enable the single-tooth cast 99 to rotate for a predetermined angle. Further, as shown in FIG. 7, drive the first swing shelf 16 by the first swing driver 18 to swing for a predetermined angle to enable the single-tooth cast 99 to face the scanning probe 42 at a different angle, and then drive the scanning probe 42 to move linearly along the slide rail 46 for further scanning. Accordingly, performing the scanning operation by repeating different rotational and swinging angles for many times can create a precise 3D model of the single-tooth cast 99. For the full-teeth cast (not shown) placed on the full-teeth cast rotating device 31, the scanning operation is similar to the single-tooth cast's 99 but different by that the second cast-holding jig 33 can be moved upwards or downwards by the lifting-and-lowering driver 37 to facilitate scanning the full-teeth cast (not shown).

Figure 8:
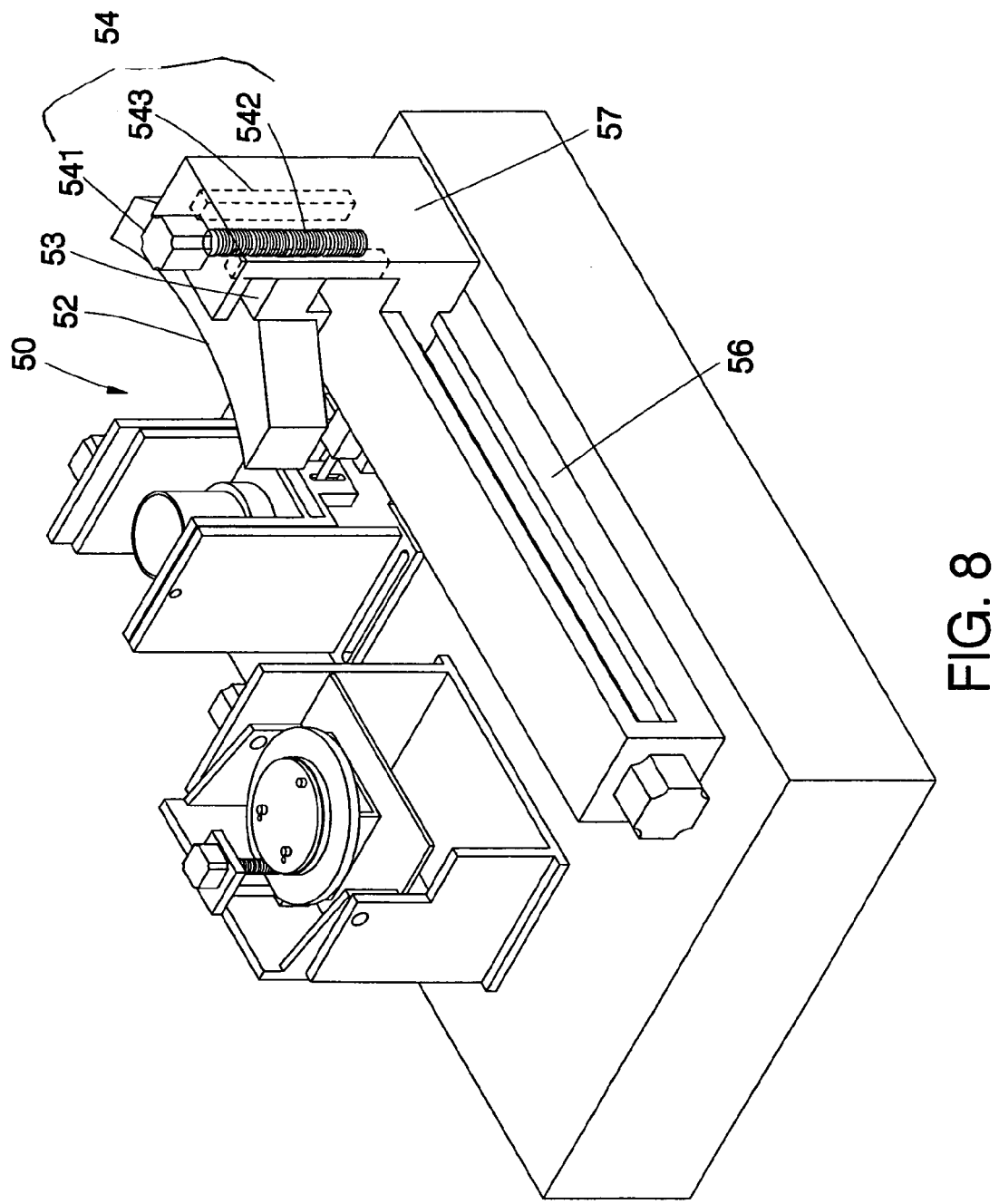
FIG. 8 is a perspective view of a second preferred embodiment of the present invention, viewing from the rear side of the present invention.

Referring to FIG. 8, the dental cast scanning apparatus 50 constructed according to a second preferred embodiment of the present invention is similar to the first preferred embodiment, but having difference as recited below.

The elevator 54 is comprised of a motor 541, a lead screw 542, a guide rail 543, and a slidable member 57 slidably mounted to the slide rail 56. The motor 541 is mounted on the slidable member 57. The lead screw 542 has an end connected with the motor 541 and a body portion thereof threadedly connected with the movable member 53. The guide rail 543 runs through the movable member 53. The scanning probe 52 can be driven to move upwards and downwards along the guide rail 543.

The operation of the dental cast scanning apparatus 50 is identical to the dental cast scanning apparatus 10 and thus no further recitation is necessary.

Figure 9:
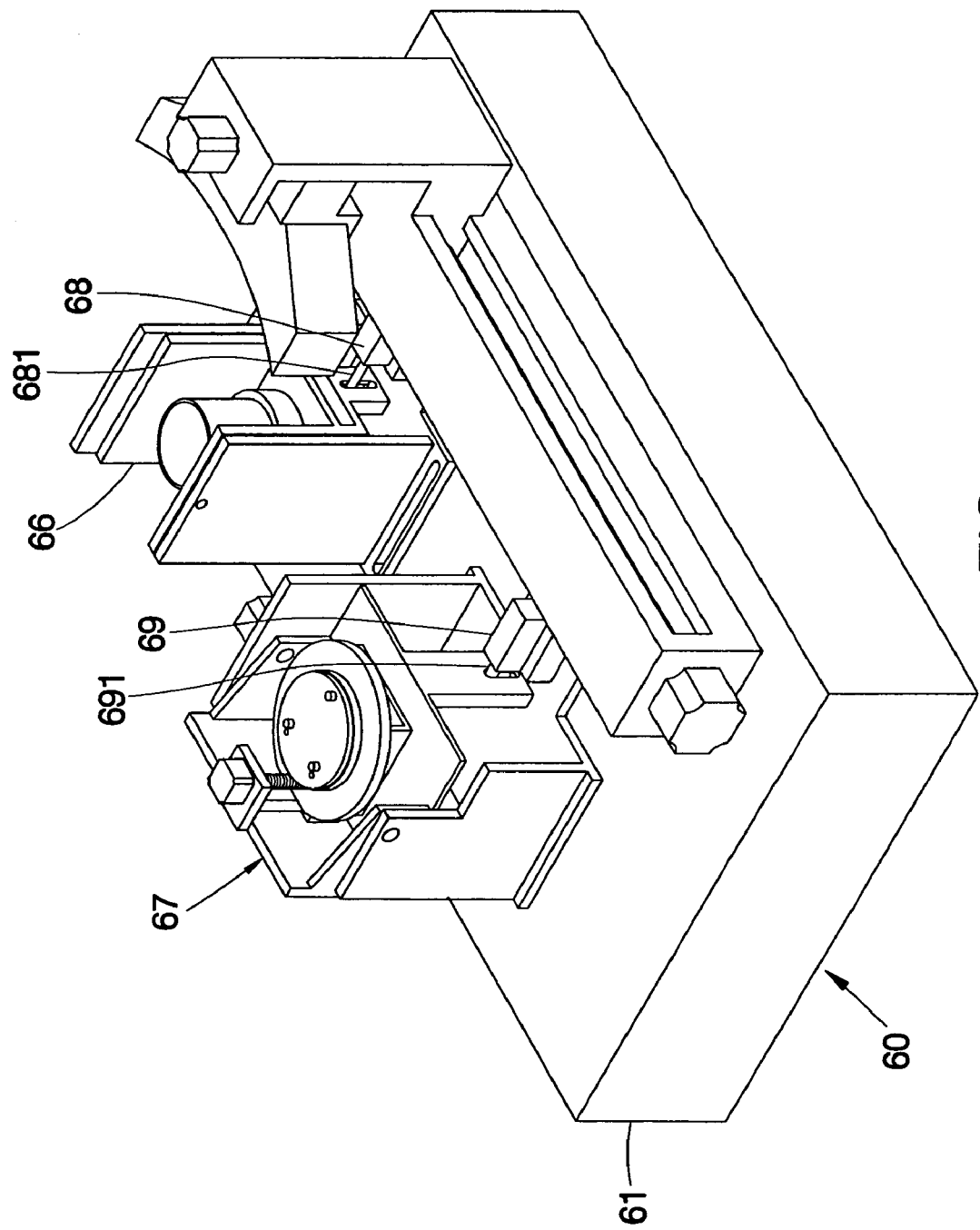
FIG. 9 is a perspective view of a third preferred embodiment of the present invention, taking from the rear side.
Figure 10:
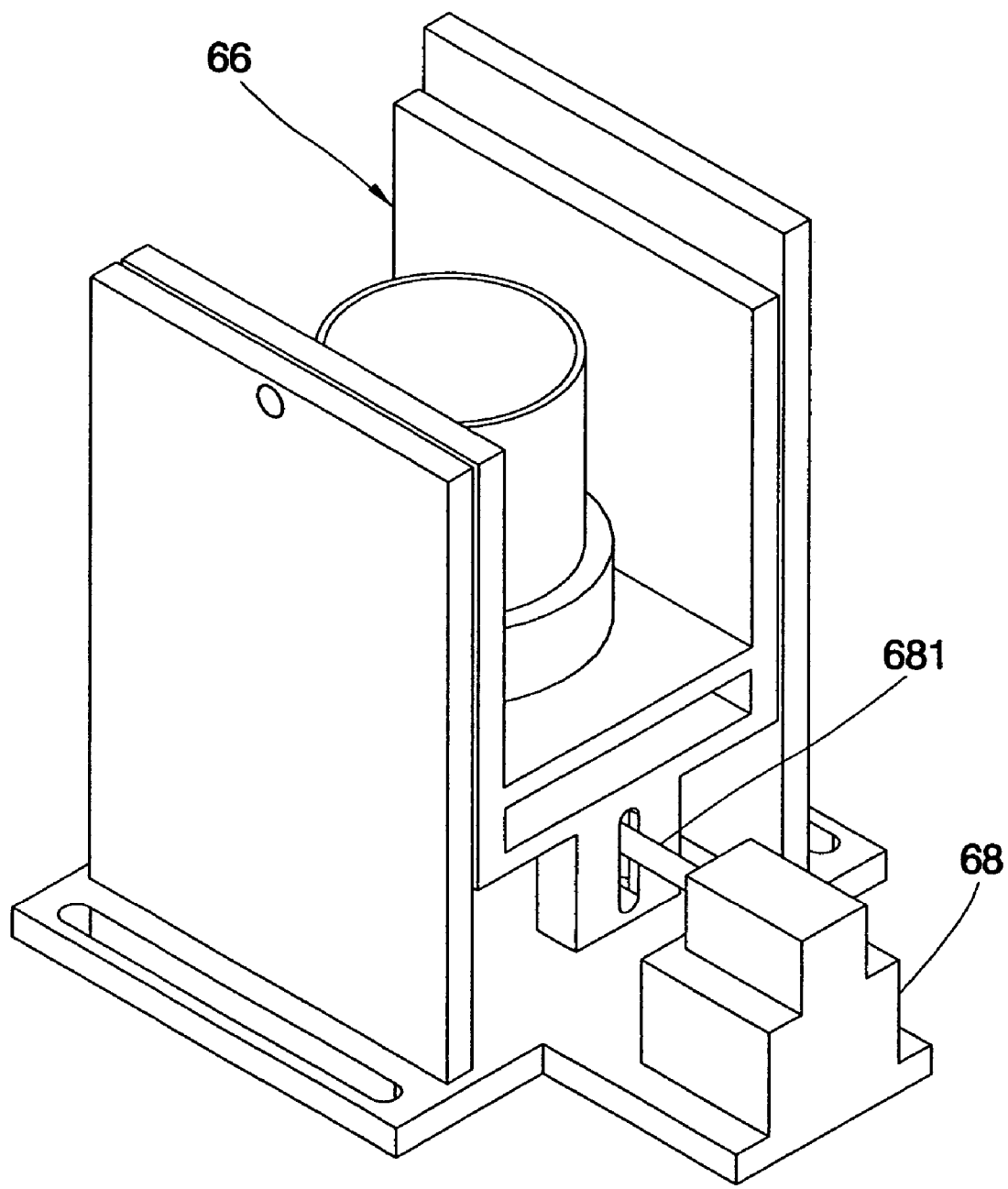
FIG. 10 is a partial perspective view of the third preferred embodiment of the present invention, showing the interrelationship between the first swing driver and the first swing shelf.

Referring to FIGS. 9 and 10, the dental cast scanning apparatus 60 constructed according to a third preferred embodiment of the present invention is similar to the first preferred embodiment, but having difference as recited below.

Each of the first and second swing driver 68 and 69 is a push-and-pull device, which is a pneumatic cylinder in this embodiment and mounted on the base 61 and having a push rod 681(691) connected with a lower part of the first (second) swing shelf 66(67), for pushing or pulling the swing shelves 66 and 67 to swing.

The operation of the dental cast scanning apparatus 60 is identical to the dental cast scanning apparatus 10 and thus no further recitation is necessary.

In conclusion, the present invention includes the following advantages.

1. More accurate scanning: The present invention can be automatically controlled to drive the rotational and swinging angles of the cast-holding jigs to avoid human errors and to render more accurate scanning outcome.

2. Simpler operation: It is as easy for the user as putting a dental cast on the single-tooth or full-teeth rotating device for scanning and then the follow-up scanning operations at any required angles can be done automatically without manual turning of the cast-holding jig.

What is claimed is:

1. A dental cast scanning apparatus comprising:
   a base;
   a single-tooth cast rotating device having a first rotatable holder, a first rotation driver, and a first cast-holding jig mounted on a top side of the first rotatable holder, said first rotatable holder being mounted on said base and connected with said first rotation driver for axial rotation driven by said first rotation driver;
   a full-teeth cast rotating device having a second rotatable holder, a second rotation driver, and a second cast-holding jig mounted on a top side of said second rotatable holder, said second rotatable holder being mounted on said base and connected with said second rotation driver for axial rotation driven by the second rotation driver; and
   a scanning unit having a scanning probe and a slide rail, said slide rail being mounted on said base and located beside said single-tooth and full-teeth cast rotating devices, said scanning probe being mounted to said slide rail for reciprocating movement along said slide rail;
   wherein said single-tooth cast rotating device further comprising a first swing driver connected with said first cast-holding rotatable holder for driving said first cast-holding rotatable holder to swing.

2. The dental cast scanning apparatus as defined in claim 1 further comprising a first rack and a U-shaped first swing shelf, said first rack having two plate-like members and spaced from each other and located upright to said base, said first swing shelf having a base plate and two side plates and swung between said two plate-like members of said first rack by at least one pivot bolt pivotally mounted to top ends of said side plates and said plate-like members, said base plate of said first swing shelf being spaced from said base for swing driven by an external force with respect to said first rack; said first cast-holding rotatable holder is mounted to said base plate of said first swing shelf; said first rotation driver is mounted under said base plate, having a driving shaft running through said base plate and connected with a bottom side of said first rotatable holder.

3. The dental cast scanning apparatus as defined in claim 2, wherein said first swing driver is a driving motor mounted to one of said plate-like members of said first rack and having a driving shaft connected with said pivot shaft for driving said first swing shelf to swing.

4. The dental cast scanning apparatus as defined in claim 2, wherein said first swing driver is a push-and-pull device having a push rod connected with a lower part of said first swing shelf for driving said first swing shelf to swing.

5. The dental cast scanning apparatus as defined in claim 1 further comprising a second rack and a U-shaped second swing shelf, said second rack having two plate-like members spaced from each other and mounted upright on said base, said second swing shelf having a base plate and two side plates and swung between said two plate-like members of said second rack by at least one pivot bolt pivotally mounted to top ends of said side plates of said second swing shelf and said plate-like members of said second rack, said base plate of said second swing shelf being spaced form said base for swing driven by an external force with respect to said second rack; said second rotation driver is mounted under said second swing shelf, having a driving shaft connected with a bottom side of said second rotatable holder.

6. The dental cast scanning apparatus as defined in claim 5, wherein said full-teeth cast rotating device further comprises a second swing driver connected with said second swing shelf for driving said second swing shelf to swing.

7. The dental cast scanning apparatus as defined in claim 1, wherein said second rotatable holder is mounted on a workbench; said second rotation driver is mounted on a bottom side of said workbench, having a driving shaft connected with said second rotatable holder; further comprising a lifting-and-lowering driver having a motor, a lead screw, and a slide rail, said motor being mounted to said second swing shelf, said lead screw having an end connected with said motor and a body portion threadedly connected with said workbench, said slide rail of said lifting-and-lowering driver being mounted to said second swing shelf, said workbench being slidably mounted on said slide rail for vertical movement driven by said motor.

8. The dental cast scanning apparatus as defined in claim 1, wherein said cast-holding jig is a detachable cup-like member having a bottom side threadedly connected with said first rotatable holder by a screw bolt.

9. The dental cast scanning apparatus as defined in claim 1, wherein said scanning unit further comprises an elevator mounted to said slide rail; said scanning probe is mounted to said elevator for movement in elevation.

10. The dental cast scanning apparatus as defined in claim 9, wherein said elevator is a pneumatic cylinder having a piston rod; said scanning probe comprises a movable member located at a rear end thereof and connected with said piston rod.

11. The dental cast scanning apparatus as defined in claim 9, wherein said scanning unit further comprises a slidable member slidably mounted to said slide rail and a movable member connected with a rear end of said scanning probe; said elevator comprises a motor, a lead screw, and a guide rail, said motor being mounted on said slidable member, said lead screw having an end connected said motor and a body portion threadedly connected with said movable member, said guide rail running through said movable member.

* * * * *